United States Patent
Yang

(10) Patent No.: US 8,859,258 B2
(45) Date of Patent: Oct. 14, 2014

(54) COMPOSITE OIL DISPLACEMENT AGENT CONTAINING A MICROORGANISM FOR OIL DISPLACEMENT AND A PREPARATION METHOD THEREOF

(76) Inventor: Yinhai Yang, Tianjin (CN)

( * ) Notice: Subject to any disclaimer, the term of this patent is extended or adjusted under 35 U.S.C. 154(b) by 0 days.

(21) Appl. No.: 13/322,567

(22) PCT Filed: Jun. 2, 2011

(86) PCT No.: PCT/CN2011/075140
§ 371 (c)(1),
(2), (4) Date: Nov. 27, 2011

(87) PCT Pub. No.: WO2012/145949
PCT Pub. Date: Nov. 1, 2012

(65) Prior Publication Data
US 2014/0038265 A1  Feb. 6, 2014

(30) Foreign Application Priority Data
Apr. 28, 2011  (CN) .......................... 2011 1 0109041

(51) Int. Cl.
*C12N 1/12* (2006.01)
*C12R 1/01* (2006.01)
*C09K 8/582* (2006.01)
*C12N 1/20* (2006.01)

(52) U.S. Cl.
CPC ... *C12N 1/20* (2013.01); *C12R 1/01* (2013.01); *C09K 8/582* (2013.01)
USPC ...................................... 435/252.1

(58) Field of Classification Search
USPC ...................................... 435/252.1
See application file for complete search history.

(56) References Cited

PUBLICATIONS

Breed et al. Bergey's Manual of Determinative Bacteriology, seventh ed. Williams and Wilkens Co. (1957) pp. 200-201.*

* cited by examiner

*Primary Examiner* — Susan Hanley
*Assistant Examiner* — Paul Martin
(74) *Attorney, Agent, or Firm* — Matthias Scholl P.C.; Matthias Scholl

(57) ABSTRACT

A composite oil displacement agent contains the following main components: 20 to 40% of microorganism, 6 to 30% of surfactant, 5 to 10% of macromolecular modifier, 1 to 5% of viscosity reducer, 1 to 5% of additive and the balance of water. The preparation method thereof comprises the steps of: in proportion by weight, adding the microorganism, the surfactant, the macromolecular modifier, the viscosity reducer, the additive, and the water to a reactor provided with a stirring device, and stirring the components for 1.5 to 2 h at room temperature to obtain the finished product.

4 Claims, No Drawings

COMPOSITE OIL DISPLACEMENT AGENT CONTAINING A MICROORGANISM FOR OIL DISPLACEMENT AND A PREPARATION METHOD THEREOF

REFERENCE TO FOREIGN APPLICATIONS

This application is based on Patent Cooperative Treaty Application No. PCT/CN2011/075140 filed on Jun. 2, 2011 which is based on Chinese Patent Application No. 201110109041.0 filed on Apr. 28, 2011.

BACKGROUND OF THE INVENTION

1. Technical Field

The present invention relates to enhanced oil recovery in tertiary oil recovery, especially to a microorganism for oil displacement and a composite oil displacement agent containing the microorganism.

2. Background

Over 40% of underground crude oil still remains in the formation after primary and secondary oil recovery; and even 80% of crude oil could remain in the formation after primary and secondary oil recovery if the formation conditions are not ideal. So far, the main oilfields in our country have undergone high water cut stage and underground crude oil has been under the discontinuous dispersed state, the oil displacement technology is mainly featured by utilizing the synergistic effect of alkaline, polymer and surfactant to reach the effects of increasing oil production increasing and reducing water, in order to enhance the recovery rate of crude oil.

Alkaline/polymer/surfactant trinary composite oil displacement system, though capable of enhancing the recovery rate of crude oil remarkably, has been accompanied by some questions in the process of large-scale industrial application: 1) the use of alkaline could lead to the precipitation of multivalent ions and the corrosion of rock and minerals, further destroying the structure of oil layer and oil well and severely damaging the formation, besides, the pump barrel needs to be cleaned once every 10 to 15 days, so the oil. recovery cost is increased; 2) the presence of alkaline can not only increase the usage of polymer dramatically, but also reduce the viscoelasticity of polymer greatly, especially the elasticity of polymer; and 3) the use of alkali could further cause the situation that the produced liquid is W/O type emulsion with higher viscosity, which not only impacts on oil well productivity, but also raises the difficulty of demulsification.

It is found by retrieval that one of three patent documents related to the present invention, CN1580486, discloses an oil displacement method, which sequentially comprises the following steps of: culturing at least one of *Bacilluscereus* HP, CGMCC No. 1141 and *Brevibacillus brevis* HT, CGMCC No. 1142 in a culture medium with crude oil as carbon source to obtain fermentation liquid; injecting the resultant fermentation liquid in the oil layer for 3 to 5 days; and then using a trinary composite system for oil displacement; according to the present invention, physical properties of crude oil are improved after microorganism fermentation liquid derived from. HP and HT is used for affecting the crude oil, the affected crude oil has reduced interfacial tension of prior trinary prescription compared with unaffected crude oil, the microorganism fermentation liquid is 2 to 12 times diluted and then added with a small amount of alkylbenzene sulfonates surfactant S1 (0.01 wt % to 0.04 wt %), the interfacial tension can reach 10-3 mN/m, the cost is greatly reduced and the crude oil has excellent stability. The patent application CN101544885 discloses a composite microorganism oil displacement agent for enhancing the oil recovery rate of crude oil, which is formed by adding mixed liquid, consisting of 1 to 8 wt. % of cereals-processing byproduct, 0.5 to 6 wt. % of wood-processing byproduct, with 5 to 10 mg/L of trace elements and 300 to 500 mg/L of polyacrylamide, wherein the agriculture/wood-processing byproducts have the particle diameter smaller than 0.5 mm. CN1504529 discloses a thick oil emulsification viscosity reducer, comprising: 1) anionic surfactant selected from the group consisting of petroleum sulfonate formaldehyde condensate and lignin sulphonate, 2) nonionic-anionic surfactant selected from the group consisting of nonionic-phosphate, nonionic-sulfate, nonionic-carboxylate and nonionic-sulfonate, and 3) water, wherein the weight ratio of the anionic surfactant to the nonionic-anionic surfactant is 1:0.2 to 10, and the water amount is 0.5 to 9 times as much as the total amount of the surfactant.

The above patent demonstrate some shortcomings: firstly, the microorganism in the above patents is stepwise added to oil recovery layer with other reagents instead of being used with other components, and secondly, no alkaline is used in the present invention.

BRIEF SUMMARY OF THE INVENTION

The present invention is generally directed toward a microorganism for oil displacement, a composite oil displacement agent containing the microorganism and a preparation method thereof.

An objective of the invention is to overcome the defects in the prior art and provide a microorganism for oil displacement and a composite oil displacement agent containing the microorganism, and the composite oil displacement agent has no alkaline, low interfacial tension and good salt resistance, and can form 10-3 mN/m of ultralow interfacial tension between oil and water on conditions of no alkaline, high temperature and high salinity.

Another objective of the invention is implemented through the following technical proposal:

A composite oil displacement agent containing the microorganism contains the following components in parts by weight:

| | |
|---|---|
| microorganism CGMCC 4670 bacterial liquid | 20 to 40% |
| surfactant | 6 to 30% |
| macromolecular modifier | 5 to 10% |
| viscosity reducer | 1 to 5% |
| additive | 1 to 5% |
| water | the balance. |

The concentration of the microorganism CGMCC 4670 bacterial liquid is 108-1010 per gram.

Further, the culture conditions of the microorganism CGMCC 4670 bacterial liquid are as follows: the weight percentages of the culture medium: 20 to 30% of sucrose, 1 to 5% of KH2PO4, 1 to 5% of MgSO4, 1 to 5% of (NH4)2SO4, 1 to 5% of corn steep liquor, 20 to 30% of nitrogen source and the balance of water, and pH is from 6 to 7.

Further, the macromolecular modifier is one or the mixture of at least two of the group consisting of sorbitolum, xylose, gelatin, reducing rubber, soluble starch, sodium methylcellulose, methylcellulose M20, hydroxyethylcellulose, hydroxypropylcellulose, polyethylene glycol 600, polyethylene glycol 6000, polyvinylpyrrolidone and polyvinyl alcohol.

Further, the surfactant comprises non-ionic surfactant and amphoteric ion surfactant, based on the total weight of the oil displacement agent, by weight percentages as below:

| | |
|---|---|
| nonionic surfactant | 3 to 15% |
| amphoteric ion surfactant | 3 to 15%. |

Further, the nonionic surfactant is one or more than two of the group consisting of isooctylphenol polyoxyethylene ether, alkylphenol ethoxylates, fatty alcohol polyoxyethylene ether, nonylphenol ethoxylates, polyethylene glycol octylphenyl ether, polyoxyethylene oleate, fatty acid polyoxyethylene ether, hexamethylene subamine and polyoxyethylene alkylamine.

Further, the amphoteric ion surfactant is one or more than two of the group consisting of carboxylic acid betaine, N-amido carboxylic acid betain, N-alkyl thiocarboxylic acid betaine and cocoamidopropyl betaine.

Further, the viscosity reducer comprises one or more than two of the group consisting of nonionic-phosphate viscosity reducer, nonionic-sulfate viscosity reducer, nonionic-carboxylate viscosity reducer and nonionic-sulfonate viscosity reducer, and laurylamidopolyethenoxy hydrocarbonether phosphate ester.

Further, the additive comprises one or more than of the group consisting of isopropanol, n-butyl, n-propyl and ethanol.

The present invention has the advantages and the positive effects:

(1) The microorganism adopted in the components of the present invention, belonging to facultative anaerobe, is a microorganism that can grow and propagate in both aerobic environment and anaerobic environment and derives from the preferred culture of the microorganisms separated from underground substances.

(2) The present invention has no alkaline contained in the components, thereby overcoming the problem that the alkaline reduces the viscoelasticity of polymer and that alkaline scale formed by the alkaline damages formation structure and flushing operation of stuck pump, so not only are the environmental protection requirements met, but the production cost is reduced.

(3) The surfactant, the macromolecular modifier and other polymers adopted in the components of the present invention are all fine chemicals resulting from industrial production, raw materials are widely available, water in the components is common clear water or can be re-injected water, environmental protection effect is good, and production cost is low.

(4) The oil displacement agent to which the present invention pertains can enhance the recovery rate of crude oil by over 30% on condition of high temperature and high salinity; and the experiment has proven that, on condition of the temperature of 45 to 75° C. and the salinity of 1500 to 20000 mg/L, the viscosity reaches 16.8 mPa/s, and the oil displacement agent can form ultralow interfacial tension, which is 10-3 mN/m, with crude oil.

(5) The experiment has proven that, on condition of oil displacement, the surfactant and the macromolecular modifier can effectively reduce the degree of freedom of polymer chain, increase hydrodynamic volume of macromolecule, and endow the solution with high viscosity so as to possess strong salt resistance; in addition, under the synergistic effect of the nonionic surfactant and the amphoteric ion surfactant, the surfactant can reduce the interfacial tension of the system effectually.

Upon reading the above description, various alternative embodiments will become obvious to those skilled in the art. These embodiments are to be considered within the scope and spirit of the subject invention, which is only to be limited by the claims which follow and their equivalents.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification.

DETAILED DESCRIPTION OF THE INVENTION

The attached drawing demonstrates an embodiment of the present invention. It is to be understood that the invention is not limited in its application to the details of the construction, and arrangement of parts illustrated in the accompanying drawings. The invention is capable of other embodiments and of being practiced or carried out in a variety of ways. It is to be understood that the phraseology and terminology employed herein are for the purpose of description and not of limitation.

Further description is made below to the technical contents of the present invention with reference to the embodiments, which are merely demonstrative instead of being limitative and cannot be employed to limit the scope of protection of the present invention.

The microorganism in the present invention is *protaminobacter alboflavus* and preserved in CGMCC (China General Microbiological Culture Collection Center), the preservation date is Mar. 15, 2011, the preservation number is CGMCC 4670, and the preservation address is Institute of Microbiology Chinese Academy of Science, No. 3, Courtyard No. 1, West Beichen Road, Chaoyang District, Beijing.

An embodiment of the culture method of the microorganism is set out as below.

About 3 ml of sterilized water is added to a strain-preserving slant test tube under sterile state, after the test tube is shaken, 1 ml of the sterilized water is sucked by a sterile suction tube and added to a triangular flask filled with 99 ml of the sterilized water, and 1 ml of the liquid in the triangular flask is added to another triangular flask filled with 9 ml of the sterilized water, and such operations are repeated until 10-6-times dilution is achieved.

0.2 ml of the above diluted solution is sucked by the sterile suction tube, put in a well-prepared culture dish and coated uniformly with a glass spreading rod, the culture dish is put in an incubator for culture for 48 hours at 28° C., and uniform, opaque and smooth orange round colonies appear on the surface of the dish. Any one of the colonies is selected under sterile state and prepared into a smear, and according to the observation under an electronic microscope, the bacterium is unicellular, sporeless and short rod-shaped. And the detection result of Gram staining is negative.

An embodiment of the fermentation process of the strain is as below:

The components of the culture medium adopted in the process of fermentation and culture are all by weight percents: 20 to 30% of sucrose, 1 to 5% of KH2PO4, 1 to 5% of MgSO4, 1 to 5% of (NH4)2SO4, 1 to 5% of corn steep liquor; 20 to 30% of common nitrogen source (e.g. beef extract, peptone, etc.) and the balance, of water, pH is regulated to 6.5, and the specific proportions are shown as below.

1. sterile working is carried out in a sterile room, the strain in the test tube is transferred to a small triangular flask which is then placed on a shaker for shaking (28° C.), tracking detection is performed to guarantee that no microbial contamination is generated in the process of culture, about 24 hours later, the strain is transferred to a large triangular flask for amplified culture when reaching the optimal growth state, and similarly, about 24 hours (28° C.) later, monitoring is performed in order to stop fermentation when the microbial contamination-free, optimal state is reached.

2. Treatment by an air system: the air system of a fermentation device is subjected to steam sterilization and then ventilated, and after being filtered and water-removed, the air reaches the sterile state, and the humidity is less than 5%.

3. Air sterilization and tank sterilization: a fermentation tank is cleaned with clear water, then closed and subjected to steam sterilization for 35 minutes at the controlled temperature of 117° C., afterwards, 23% of sucrose, 2% of KH2PO4, 1% of MgSO4, 2% of (NH4)2SO4, 2% of corn steep liquor, 20% of beef extract are adopted according to the formula (by weight percents), pH is regulated to 6.5 (pH regulation: if the tap water used has good quality, pH does not need to be regulated after the culture medium adopting this formula is prepared. If pH is not appropriate, saturated NaOH aqueous solution, or saturated concentrated hydrochloric acid can be used for pH regulation prior to the sterilization of the culture medium), after the above raw materials are prepared in proportions, the tank is heated up to 117° C., and after the temperature is maintained for 30 minutes, the tank is cooled to the temperature as required by fermentation.

4. The bacteria liquid cultured in the above shake flask is transferred to a small fermentation tank (which has been subjected to air sterilization and tank sterilization) on condition of sterile working, sterile air is fed to the small fermentation tank for about 24 hours (28° C.), the strain is transferred to a large fermentation tank (which has been subjected to air sterilization and tank sterilization) for amplified culture when reaching the optimal growth state, sterile air is fed to the large fermentation tank for about 24 hours (28° C.), fermentation is stopped and the fermented product is removed out of the tank and loaded when the microbial contamination-free, optimal state is reached.

5. Inspection and evaluation: the fermented product shall meet the quality standard in two aspects: the product is milk-white and liquid in appearance and has fishy odor slightly; according to the concentration detection, the number is required to be more than 108 per gram and the content of the microbial contamination is required to be lower than 10% of the total amount of cell.

All the microorganisms adopted in the embodiments below are the above preserved strain, and the microorganism bacteria liquid has the concentration of 108 per gram and above.

An embodiment of a composite oil displacement agent of the present invention contains the components and the weights thereof as below:

| microorganism bacteria liquid | 30.0 g |
| polyoxyethylene oleate | 1.0 g |
| isooctylphenol polyoxyethylene ether | 15.0 g |
| methylcellulose M20 | 5.0 g |
| nonionic-phosphate viscosity reducer | 7.0 g |
| isopropanol | 2.0 g |
| clear water | the balance, | wherein the methylcellulose M20 is macromolecular modifier and may also be replaced by one or the mixture of more than two of the group consisting of sorbitolum, xylose, gelatin, reducing rubber, soluble starch, sodium methylcellulose, hydroxyethylcellulose, hydroxypropylcellulose, polyethylene glycol 600, polyethylene glycol 6000, polyvinylpyrrolidone and polyvinyl alcohol, which are all commercially available.

The isooctylphenol polyoxyethylene ether and the polyoxyethylene oleate are nonionic surfactants and may also be replaced by one or more than two of the group consisting of alkylphenol ethoxylates, fatty alcohol polyoxyethylene ether, nonylphenol ethoxylates, polyethylene glycol octylphenyl ether, fatty acid polyoxyethylene ether, hexamethylene subamine and polyoxyethylene alkylamine, which are all primary products.

The nonionic-phosphate viscosity reducer is viscosity reducer, and the viscosity reducer further comprises one or more than two of the group consisting of nonionic-phosphate viscosity reducer, nonionic-sulfate viscosity reducer, nonionic-carboxylate viscosity reducer and nonionic-sulfonate viscosity, reducer, and, laurylamidopolyethenoxy hydrocarbonether phosphate ester, which are all commercially available.

The isopropanol is additive and may also be replaced by one or more than two of the group consisting of isopropanol, n-butyl, n-propyl and ethanol.

The preparation method of the composite oil displacement agent comprises the steps of: adding 30.0 g of the microorganism, 15.0 g of the isooctylphenol polyoxyethylene ether, 5.0 g of the methylcellulose M20, 1.0 g of the polyoxyethylene oleate, 7.0 g of the nonionic-phosphate viscosity reducer, 2.0 g of the isopropanol and the balance of clear water to, a mixer provided with a stirring device, and stirring the components for 2 h at room temperature to obtain the finished product of molecular composite surfactant.

The determination of oil-water interfacial tension system:

| the amount of surfactant | 0.1% concentration |
| polyacrylamide and clear water (or re-injected water) | 1000 ppm |
| crude oil | detection amount |

The detection result, of the experiment: the viscosity is determined to be 16.5 mPa·S by a DV-II Brookfield viscometer (UL connector) at the rotating speed of 30 r/min on condition of the temperature from 45 to 75° C. and the salinity from 1500 to 20000 mg/L, and the minimal interfacial tension is determined to be 6×10-3 mN/m by a RX-500C interfacial tension instrument at the rotating speed of 5000 r/min in accordance with SY/T5370-1999 Determination Method and Evaluation Standard for Surface and Interfacial Tension.

A second embodiment of a composite oil displacement agent of the present invention contains the components and the weights thereof as below.

| microorganism bacteria liquid | 40.0 g |
| fatty alcohol polyoxyethylene ether | 10.0 g |
| betaine | 4.0 g |
| polyvinylpyrrolidone | 4.5 g |
| reducing rubber | 3.0 g |
| hexamethylene subamine | 3.0 g |
| nonionic-sulfate viscosity reducer | 3.0 g |
| n-butanol | 2.0 g |
| clear water | the balance, | wherein the betaine is amphoteric ion surfactant and may also be replaced by one or more than two of the group consisting of carboxylic acid betaine, N-amido carboxylic acid betain, N-alkyl thiocarboxylic acid betaine and cocoamidopropyl betaine, which are all primary products.

An embodiment of the preparation method of this embodiment of the composite oil displacement agent comprises the steps of: adding 40.0 g of the microorganism, 10 g of the fatty alcohol polyoxyethylene ether; 4.0 g of the betaine, 4.5 g of the polyvinylpyrrolidone, 3.0 g of the reducing rubber, 3.0 g of the hexamethylene subamine, 2.0 g of the n-butanol and the balance of clear water to a mixer provided with a stirring device, and stirring the components for 2 h at room temperature.

The determination of oil-water interfacial tension system:

| the amount of surfactant | 0.1% concentration |
| polyacrylamide and clear water (or re-injected water) | 1000 ppm |
| crude oil | detection amount. |

The detection result of the experiment: the viscosity is determined to be 10.5 mPa·S by a DV-II Brookfield viscometer (UL connector) at the rotating speed of 30 r/min on condition of the temperature from 45 to 75° C. and the salinity from 1500 to 20000 mg/L, and the minimal interfacial tension is determined to be $5 \times 10-3$ mN/m by a RX-500C interfacial tension instrument at the rotating speed of 5000 r/min in accordance with SY/T5370-1999 Determination Method and Evaluation Standard for Surface and Interfacial Tension.

An additional embodiment of the composite oil displacement agent of the present invention contains the components and the weights thereof as below:

| microorganism bacteria liquid | 40.0 g |
| reducing rubber | 1.0 g |
| betaine | 16.0 g |
| laurylamidopolyethenoxy hydrocarbonether phosphate ester | 4.0 g |
| n-butanol | 3.0 g |
| clear water | the balance. |

An embodiment of the preparation method of the composite oil displacement agent comprises the steps of: adding 40.0 g of the microorganism, 1.0 g of the reducing rubber, 16.0 g of the betaine, 4.0 g of the laurylamidopolyethenoxy hydrocarbonether phosphate ester, 3.0 g of the n-butanol and the balance of clear water to a mixer provided with a stirring device, and stirring the components for 2 h at room temperature.

The determination of oil-water interfacial tension system:

| the amount of surfactant | 0.1% concentration |
| polyacrylamide and clear water (or re-injected water) | 1200 ppm |
| crude oil | detection amount |

The detection result of the experiment: the viscosity is determined to be 18.5 mPa·S by a DV-II Brookfield viscometer (UL connector) at the rotating speed of 30 r/min on condition of the temperature from 45 to 75° C. and the salinity from 1500 to 20000 mg/L, and the minimal interfacial tension is determined to be $3 \times 10-3$ mN/m by a RX-500C interfacial tension instrument at the rotating speed of 5000 r/min in accordance with SY/T5370-1999 Determination Method and Evaluation Standard for Surface and Interfacial Tension.

The present invention is based on the principal that the composite oil displacement agent is the oil displacement system obtained by compounding microorganism and surfactants in proportion, by utilizing saturated alkane (paraffin) of a long chain of the microorganism, the viscosity and the components of crude oil are changed through the reduction of paraffin content and through derivative light components so as to increase the fluidity of formation fluids into oil well and further achieve the effects of plug removal and paraffin removal for reservoir fluids; simultaneously, the synergistic effect of a plurality of surfactants are used to reduce oil-water interfacial tension, and the purpose of enhancing the recovery rate of crude oil is reached, by means of the co-action of both.

The above detailed description to the microorganism, the surfactant composite oil displacement agent and the preparation method thereof with reference to the embodiments are intended to be demonstrative instead of being limitative, several embodiments can be made within the limited scope, therefore, variations and modifications without departing from the overall concept of the present invention shall fall within the scope of protection of the present invention.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification.

What is claimed is:

1. A composite oil displacement agent, comprising the following components in parts by weight:
    from 20 to 40% of *Protaminobacter alboflavus* microorganism CGMCC 4670 bacterial liquid;
    from 6 to 30% of a surfactant;
    from 5 to 10% of a macromolecular modifier;
    from 1 to 5% of a viscosity reducer;
    from 1 to 5% of an additive; and
    the balance of water;
    wherein a concentration of the microorganism in CGMCC 4670 bacterial liquid is between 108 and 1010 bacteria per gram, and the macromolecular modifier is one or more than two of the group consisting of sodium methylcellulose, methylcellulose M20, hydroxyethylcellulose, hydroxypropylcellulose, polyethylene glycol 600, polyethylene glycol 6000, polyvinylpyrrolidone and polyvinyl alcohol.

2. A composite oil displacement agent, comprising the following components in parts by weight:
    from 20 to 40% of *Protaminobacter alboflavus* microorganism CGMCC 4670 bacterial liquid;
    from 6 to 30% of a surfactant;
    from 5 to 10% of a macromolecular modifier;
    from 1 to 5% of a viscosity reducer;
    from 1 to 5% of an additive; and
    the balance of water;
    wherein a concentration of the microorganism in CGMCC 4670 bacterial liquid is between 108 and 1010 bacteria per gram, and the surfactant comprises non-ionic surfactant and amphoteric ion surfactant, based on the total weight of the oil displacement agent, by weight percentages as below:
    from 3 to 15% of nonionic surfactant; and
    from 3 to 15% of amphoteric ion surfactant, wherein the nonionic surfactant is one or more than two of the group consisting of isooctylphenol polyoxyethylene ether, alkylphenol ethoxylates, fatty alcohol polyoxyethylene ether, nonylphenol ethoxylates, polyethylene glycol octylphenyl ether, polyoxyethylene oleate, fatty acid polyoxyethylene ether, hexamethylene subamine and polyoxyethylene alkylamine.

3. The composite oil displacement agent according to claim 2, wherein the amphoteric ion surfactant is one or more than two of the group consisting of carboxylic acid betaine, N-amido carboxylic acid betain, N-alkyl thiocarboxylic acid betaine and cocoamidopropyl betaine.

4. A composite oil displacement agent, comprising the following components in parts by weight:
   from 20 to 40% of *Protaminobacter alboflavus* microorganism CGMCC 4670 bacterial liquid;
   from 6 to 30% of a surfactant;
   from 5 to 10% of a macromolecular modifier;
   from 1 to 5% of a viscosity reducer;
   from 1 to 5% of an additive; and
   the balance of water;
   wherein a concentration of the microorganism in CGMCC 4670 bacterial liquid is between 108 and 1010 bacteria per gram, and the additive comprises one or more than two of the group consisting of: isopropanol, n-butanol, n-propanol and ethanol, wherein the macromolecular modifier is one or more than two of the group consisting of sodium methylcellulose, methylcellulose M20, hydroxyethylcellulose, hydroxypropylcellulose, polyethylene glycol 600, polyethylene glycol 6000, polyvinylpyrrolidone and polyvinyl alcohol.

* * * * *